(12) United States Patent
Frank et al.

(10) Patent No.: US 8,195,308 B2
(45) Date of Patent: Jun. 5, 2012

(54) IMPLANTABLE HERMETICALLY SEALED STRUCTURES

(75) Inventors: Jeremy Frank, San Francisco, CA (US); Vladimier Gelfandbein, Mountain View, CA (US); Marc Jensen, Los Gatos, CA (US); Mark J. Zdeblick, Portola Valley, CA (US); Benedict James Costello, Berkeley, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 685 days.

(21) Appl. No.: 11/794,016

(22) PCT Filed: Dec. 22, 2005

(86) PCT No.: PCT/US2005/046815
§ 371 (c)(1),
(2), (4) Date: Apr. 2, 2008

(87) PCT Pub. No.: WO2006/069323
PCT Pub. Date: Jun. 29, 2006

(65) Prior Publication Data
US 2008/0312726 A1  Dec. 18, 2008

Related U.S. Application Data

(60) Provisional application No. 60/638,692, filed on Dec. 22, 2004, provisional application No. 60/655,609, filed on Feb. 22, 2005, provisional application No. 60/681,919, filed on May 16, 2005, provisional application No. 60/697,789, filed on Jul. 8, 2005.

(51) Int. Cl.
*A61N 1/05* (2006.01)

(52) U.S. Cl. .............. 607/122; 607/1; 607/2; 607/116; 607/119; 600/372; 600/393; 600/395

(58) Field of Classification Search .............. 607/1–2, 607/116, 119, 122; 600/372, 393, 395
See application file for complete search history.

(56) References Cited

U.S. PATENT DOCUMENTS

| | | |
|---|---|---|
| 3,943,936 A | 3/1976 | Rasor et al. |
| 4,815,469 A | 3/1989 | Chambers |
| 5,515,848 A | 5/1996 | Corbett, III et al. |
| 5,551,553 A | 9/1996 | Hay |
| 5,772,108 A | 6/1998 | Ruggiere, Sr. et al. |
| 5,963,429 A | 10/1999 | Chen |
| 5,983,126 A | 11/1999 | Wittkampf |
| 5,999,848 A | 12/1999 | Gord et al. |
| 6,051,017 A | 4/2000 | Loeb et al. |
| 6,214,032 B1 * | 4/2001 | Loeb et al. ......... 607/1 |
| 6,259,937 B1 | 7/2001 | Schulman et al. |
| 6,266,567 B1 | 7/2001 | Ishikawa et al. |
| 6,473,653 B1 | 10/2002 | Schallhorn et al. |
| 6,631,555 B1 | 10/2003 | Youker et al. |

(Continued)

FOREIGN PATENT DOCUMENTS

WO  9737720  10/1997

(Continued)

*Primary Examiner* — Carl H Layno
*Assistant Examiner* — Deborah Malamud
(74) *Attorney, Agent, or Firm* — Bozicevic, Field & Francis LLP; Bret E. Field

(57) ABSTRACT

Implantable hermetically sealed structures and methods for making the same. Devices, systems and kits including the hermetically sealed structures, as well as methods of using such devices and systems are included.

23 Claims, 13 Drawing Sheets

U.S. PATENT DOCUMENTS

| | | |
|---|---|---|
| 7,096,070 B1 | 8/2006 | Jenkins et al. |
| 7,673,679 B2 | 3/2010 | Harrison et al. |
| 2002/0165589 A1 | 11/2002 | Imran et al. |
| 2003/0036773 A1* | 2/2003 | Whitehurst et al. ............. 607/3 |
| 2003/0233134 A1 | 12/2003 | Greenberg et al. |
| 2004/0193021 A1 | 9/2004 | Zdeblick et al. |
| 2005/0038481 A1 | 2/2005 | Chinchoy et al. |

FOREIGN PATENT DOCUMENTS

| | | |
|---|---|---|
| WO | 02089655 | 11/2002 |
| WO | WO2006029090 A2 | 3/2006 |
| WO | WO2006042039 A2 | 4/2006 |

* cited by examiner

IMPLANTABLE HERMETICALLY SEALED STRUCTURES

CROSS-REFERENCE TO RELATED APPLICATIONS

This application is a 371 application of PCT application serial no. PCT/US2005/046815 filed Dec. 22, 2005, which application pursuant to 35 U.S.C. §119(e), claims priority to the filing dates of: U.S. Provisional Patent Application Ser. No. 60/638,692 filed Dec. 22, 2004; U.S. Provisional Patent Application Ser. No. 60/655,609 filed Feb. 22, 2005; U.S. Provisional Patent Application Ser. No. 60/681,919 filed May 16, 2005; and U.S. Provisional Patent Application Ser. No. 60/697,789 filed Jul. 8, 2005; the disclosures of which are herein incorporated by reference.

BACKGROUND

Prior attempts to fabricate a microchip or microsensor assemblies that could survive for long periods of time in saline or high humidity environments have failed due to a number of factors. This challenge is particularly critical in implantable medical devices.

This challenge has been met in the case of implantable heart devices by providing core electronics and all controller chips in a "pacemaker can", which is located outside the heart. This relatively large device allows the full hermeticity protection of core electrical components. However, its size precludes the use of this protection at a site within the heart. This limitation has challenged development of cardiac devices which can provide microprocessing at the site of the sensing or actuation.

Important avenues of medical device development would be opened if an on-site packaging would become available which would protect key electrical, mechanical and/or actuation components from the effects of leakage of local materials into the devices.

SUMMARY

Implantable hermetically sealed structures and methods for making and using the same are provided. Also provided are devices, systems and kits including the hermetically sealed structures, as well as methods of using such devices and systems. The inventive miniaturized, corrosion resistant hermetic package provides, for the first time, protection for an effector, e.g., that includes an integrated circuit (IC), in long term contact with saline, blood or other body fluid in a size form that is orders of magnitude smaller than previously available designs. This packaging has, by design, a uniquely miniaturized form factor. The present invention allows the practical development of miniaturized, implantable medical devices for days, months, and even years of practical, reliable use.

Aspects of the invention include implantable hermetically sealed structures dimensioned to be placed inside a lead, e.g., a cardiovascular lead, left ventricular lead, epicardial lead, etc. In certain embodiments, the structure comprises an effector, e.g., an actuator (such as an electrode) and/or a sensor. In certain embodiments, the effector includes an integrated circuit. Embodiments of the structures are configured to remain hermetically sealed in a saline environment for at least 10 years.

Embodiments of the structures include an in vivo corrosion resistant holder having at least one conductive feedthrough; and a sealing layer; wherein the sealing layer and holder are configured to define a hermetically sealed volume. The conductive feedthrough may be a metal (e.g., platinum, iridium etc.), an alloy of metal and a semiconductor, a nitride, a semiconductor or some other convenient material. In certain embodiments, the corrosion resistant holder comprises silicon or a ceramic. In certain embodiments, the corrosion resistant holder comprises walls that are at least about 1 μm thick, such as at least about 50 μm thick, and ranges in certain embodiments from about 1 to about 125 μm, including from about 25 to about 100 μm, e.g., about 75 μm. In certain embodiments, the sealing layer is metallic, such as a noble metal, e.g., platinum or alloy thereof, containing sealing layer. In certain embodiments, the sealing layer is at least about 0.5 μm thick, such as at least about 2.0 μm thick, including at least about 20 μm thick and ranges in certain embodiments from about 0.5 to about 100 μm, such as from about 1 to about 50 μm, e.g., about 10 μm. In certain embodiments, the structure further includes an insulative material present in the hermetically sealed volume. In certain embodiments, the hermetically sealed volume ranges from about 1 pl to about 1 ml. In certain embodiments the structure is electrically coupled to at least one elongated conductive member, where the elongated conductive member may be electrically coupled to a control unit, such as one that is present in a pacemaker can.

Aspects of the invention further include methods of making a hermetically sealed structure, where the methods include: positioning an effector through an opening in an in vivo corrosion resistant holder; and fabricating a sealing layer over the opening to seal the effector in the holder in a hermetically sealed volume; wherein said method further comprises producing a conductive feedthrough in said holder that is electrically coupled to said effector, e.g., by filling a passage in said holder with a conductive material and further melting a solder material positioned between said effector and said conductive feedthrough or filling a passage in the holder with a conductive material and contacting the effector in a single process step. In certain embodiments, the methods further include planarizing said holder prior to producing said sealing layer. In certain embodiments the holder is present in a structure that includes multiple chip holders and said the further includes separating the multiple chip holders to produce the hermetically sealed structure.

Aspects of the invention further include implantable medical devices that include a hermetically sealed structure of the invention. In certain embodiments, the structure is present in a lead, such as a cardiovascular lead, a left ventricular lead or an epicardial lead. In certain embodiments, the device is chosen from a neurological device, a muscular device, a gastrointestinal device, a skeletal device, a pulmonary device, an ophthalmic device and an auditory device. In certain embodiments, the device includes two or more of the hermetically sealed structures.

Aspects of the invention further include methods of implanting an implantable medical device of the invention into a subject; and using said effector of said implanted medical device.

Also included are systems and kits that include a hermetically sealed structure according to the invention; and a control unit.

DETAILED DESCRIPTION

Figure 1:
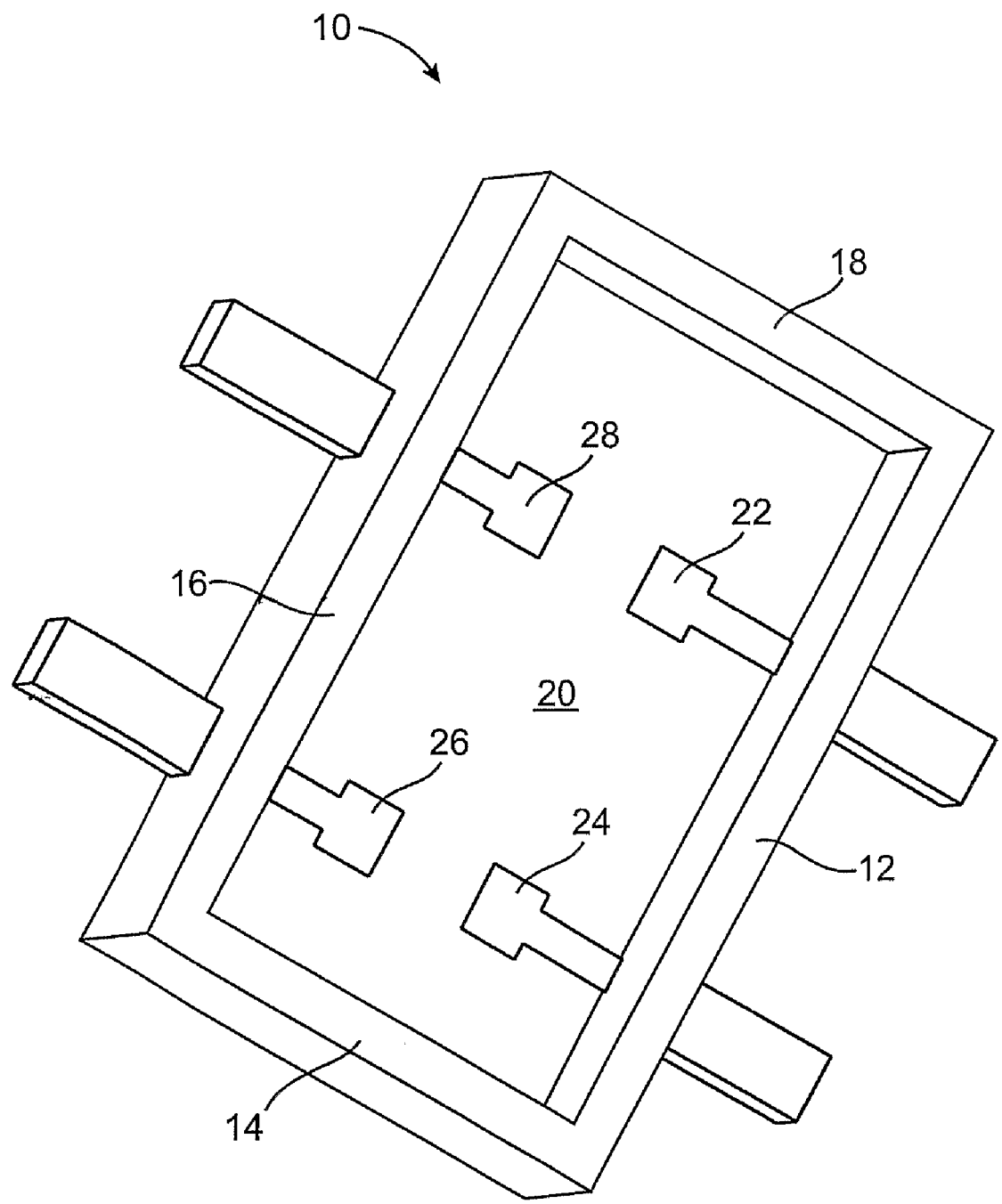
FIG. 1 provides a three-dimensional representation of an in vivo corrosion resistant holder according to an embodiment of the invention.

As summarized above, aspects of the invention provide implantable hermetically sealed structures and methods for making and using the same. Also provided are devices, systems and kits including the hermetically sealed structures, as well as methods of using such devices and systems.

Before the present invention is described in greater detail, it is to be understood that this invention is not limited to particular embodiments described, and as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing aspects of the invention, embodiments of hermetically sealed structures are reviewed first in greater detail. Next, embodiments of production protocols for manufacturing the hermetically sealed structures are reviewed. Embodiments of devices and devices, such as implantable medical devices and systems, that include hermetically sealed structures of the invention are then described, as well as methods of using such devices in different applications. Also provided is a description of kits that incorporate aspects of the invention.

Hermetically Sealed Structures

As summarized above, embodiments of the invention include implantable hermetically sealed structures. As the hermetically sealed structures are implantable, the structure can functionally survive (i.e., without substantial, if any, compromise of the function) for a substantial period in a saline environment, such as in a physiological environment in which they are in contact with blood, and/or tissue. As such, once implanted, the structures do not deteriorate in terms of function, e.g., as determined by function of an effector sealed inside of the structure, for a period of at least about 2 or more days, such as at least about 1 week, at least about 4 weeks, at least about 6 months, at least about 1 year or longer, e.g., at least about 5 years or longer. In certain embodiments, the hermetically sealed structures provide hermetic protection to effectors present therein when implanted at a physiological site for a period ranging from about 1 to about 80 years or longer, such as from about 5 to about 70 years or longer, and including for a period ranging from about 10 to about 50 years or longer. Furthermore, the integrity of the hermetic seal is maintained despite the implanted structure being subjected to significant voltage variations, e.g., ranging from about 0.1V to about 100 V, such as from about 1V to about 5V. Because the hermetically sealed structures are able to survive in high humidity, salt spray environments, they have many important applications outside use in the human body, e.g., in other high reliability assemblies that would be subject to salt water and/or high humidity. However, for ease of description only, aspects of the hermetically sealed structures are further described herein primarily in terms of implantable medical device embodiments.

In embodiments of the invention, the hermetically sealed structures are dimensioned to be placed inside a cardiovascular lead. By "dimensioned to be placed inside of a cardiovascular lead" is meant that the hermetically sealed structures have a sufficiently small size (i.e., form factor) such that they can be positioned inside of a cardiovascular lead. In certain embodiments, the hermetically sealed structures have a longest dimension, e.g., length, width or height, ranging from about 0.05 mm to about 20 mm, such as from about 0.2 mm to about 5 mm, including from about 0.5 mm to about 2 mm. As such, embodiments of the structures have a size that is orders of magnitude smaller than previously available designs. Accordingly, embodiments of the structures allow the practical development of miniaturized, implantable medical devices for days, months, and even years of practical, reliable use.

In certain embodiments, the hermetically sealed structure includes a hermetically sealed volume that houses one or more effectors. The term "effector" is generally used herein to refer to sensors, activators, sensor/activators, actuators (e.g., electromechanical or electrical actuators) or any other device that may be used to perform a desired function. In some embodiments, for example, effectors include a transducer and a processor (e.g., in the form of an integrated circuit (digital or analog). As such, embodiments of the invention include ones where the effector comprises an integrated circuit. The term "integrated circuit" (IC) is used herein to refer to a tiny complex of electronic components and their connections that is produced in or on a small slice of material, i.e., chip, such as a silicon chip. In certain embodiments, the IC is an IC as described in PCT Patent Application Serial No. PCT/US2005/031559 titled "Methods And Apparatus For Tissue Activation And Monitoring" filed on Sep. 1, 2005, the disclosure of which is herein incorporated by reference.

The effectors may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. As such, the effectors may be sensors, e.g., temperature sensors, accelerometers, ultrasound transmitters or receivers, voltage sensors, potential sensors, current sensors, etc. Alternatively, the effectors may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like.

Some of the present inventors have developed Doppler, pressure sensors, additional wall motion, and other cardiac parameter sensing devices, which effector devices or at least components thereof can be hermetically sealed according to embodiments of the invention, as desired. Some of these are embodied in currently filed provisional applications; "One Wire Medical Monitoring and Treating Devices", U.S. Provisional Patent Application No. 60/607,280 filed Sep. 2, 2004, U.S. patent application Ser. No. 11/025,876 titled "Pressure Sensors having Stable Gauge Transducers"; U.S. patent application Ser. No. 11/025,366 "Pressure Sensor Circuits"; U.S. patent application Ser. No. 11/025,879 titled "Pressure Sensors Having Transducers Positioned to Provide for Low Drift"; U.S. patent application Ser. No. 11/025,795 titled "Pressure Sensors Having Neutral Plane Positioned Transducers"; U.S. patent application Ser. No. 11/025,657 titled "Implantable Pressure Sensors"; U.S. patent application Ser. No. 11/025,793 titled "Pressure Sensors Having Spacer Mounted Transducers"; "Stable Micromachined Sensors" U.S. Provisional Patent Application 60/615,117 filed Sep. 30, 2004, "Amplified Compliant Force Pressure Sensors" U.S. Provisional Patent Application No. 60/616,706 filed Oct. 6, 2004, "Cardiac Motion Characterization by Strain Measurement" U.S. Provisional Patent Application filed Dec. 20, 2004, and PCT Patent Application entitled "Implantable Pressure Sensors" filed Dec. 10, 2004, "Shaped Computer Chips with Electrodes for Medical Devices" U.S. Provisional Patent Application filed Feb. 22, 2005; "Fiberoptic Cardiac Wall Motion Timer" U.S. Provisional Patent Application 60/658,445 filed Mar. 3, 2005; "Cardiac Motion Detection Using Fiberoptic Strain Gauges" U.S. Provisional Patent Application 60/667,749 filed Mar. 31, 2005. These applications are incorporated in their entirety by reference herein.

Aspects of the invention include hermetically sealed structures that include: an in vivo corrosion resistant holder having at least one conductive feedthrough; and a sealing layer; where the sealing layer and the holder are configured to define a hermetically sealed volume, e.g., in which one or more effectors is present. Selection of appropriate dimensions and/or materials for these elements, as reviewed in greater detail below, provides for the implantable functionality of the hermetically sealed structures, e.g., as reviewed above.

In certain embodiments, the in vivo corrosion resistant holder is a structure that is configured to hold an effector(s), e.g., such that the effector is bounded on all but one side by the walls of the holder. In certain embodiments, the holder includes side walls and a bottom. The holder may have a variety of different configurations so long as it is able to contain the effector of interest in a manner such that the effector is held in a volume bounded on all but one side. Accordingly, the shape of the holder may be square, circular, ovoid, rectangular, or some other shape as desired.

The holder may be fabricated from a variety of different materials, including, but not limited to: silicon (e.g., single crystal, polycrystalline, etc), ceramics, e.g., silicon carbide, alumina, aluminum oxide, aluminum nitride, boron nitride, beryllium oxide, among others; diamond-like carbon, sintered materials, etc. In certain embodiments, the holder is fabricated from a material that is transparent to light, at least in a certain wavelength range, e.g., infrared light. Virtually any ceramic can be employed for the holder as long as the ceramic selected meets the corrosion requirements of a particular assembly and its intended environment. When multiple materials are employed, the coefficients of thermal expansion may be taken into account in the material selection so that the materials do not negatively impact the functionality of an effector sealed in the structure.

In certain embodiments, the holders include one on or more conductive feedthroughs positioned in a wall or bottom of the holder. The conductive feedthrough is, in certain embodiments, a relatively thick conductive material present in the bottom of the holder. By relatively thick is meant that it has a thickness ranging from about 0.001 mm to about 1 mm, such as from about 0.01 mm to about 0.1 mm. In certain embodiments, the thickness ranges from about 12 to about 375 μm, such as from about 20 to about 125 μm, e.g., 75 μm. The conductive feedthrough may be fabricated from a variety of different materials. Suitable materials of interest include, but are not limited to: metals, e.g., noble metals and alloys thereof, such as gold (Au), silver (Ag), nickel (Ni), Osmium (Os), palladium (Pd), platinum (Pt), rhodium (Rh), and iridium (Ir), where in certain embodiments the noble metal is not gold or an alloy thereof. In yet other embodiments, the conductive material is a gold alloy. Metals that may be combined with a noble metal in the production of suitable noble metal alloys include, but are not limited to other noble metals, titanium (Ti), chromium (Cr), tungsten (W), and the like. Also of interest as conductive materials are alloys of noble metals with semiconductor materials, e.g., metal silicides, as reviewed in greater detail below.

In certain embodiments, an in vivo corrosion resistant holder has structure as depicted three-dimensionally in FIG. 1. In FIG. 1, in vivo corrosion resistant holder 10 is a rectangular container that includes four walls, 12, 14, 16 and 18, and bottom 20. As such, the walls and bottom of the holder define a contained volume that is bounded on all but one side with material. The width of the walls and thickness of the bottom may vary and, in certain embodiments, is selected to be sufficient to provide for the desired corrosion resistance for the time the structure is to be present in the in vivo environment. In certain embodiments, the width of the walls and thickness of the bottom range from about 0.001 mm to about 10 mm, such as from about 0.01 mm to about 1.0 mm, including from about 0.025 mm to about 0.25 mm. The volume contained on all but one side in the structure shown in FIG. 1 may vary, e.g., depending on whether a single or multiple effectors are to be sealed in the structure, and in certain embodiments ranges from about 1 pl to about 1 ml, such as from about 1 μl to about 100 μl, including from about 0.1 μl to about 1 μl. Also shown in the bottom surface of holder 10 are four distinct conductive feedthroughs, 22, 24, 26 and 28, which provide for conductive connection from the inner bottom surface of the holder to external connector elements 32, 34, 36 and 38. While the holder is depicted as having four different conductive feedthroughs, any desired number of feedthroughs may be present, e.g., 1 or more, as reviewed above, such as from about 1 to about 1000, e.g., from about 2 to about 100, including from about 3 to about 10. Furthermore, the conductive feedthroughs may be fabricated from any convenient material, e.g., noble metal such as platinum or alloy thereof, silicide such as metal suicide (as reviewed in greater detail below), etc. As reviewed in greater detail below, the holder can be fabricated using a number of different protocols, including planar processing protocols in which structures are built up and/or removed from a surface or surfaces of an initially planar substrate using a variety of different material removal and deposition protocols applied to the substrate in a sequential manner.

In the hermetically sealed structures of embodiments of the invention, the open end of the holder is sealed with a sealing layer. The sealing layer is a layer that is of sufficient thickness fabricated from a suitable material to define a hermetically sealed volume bounded on one side, e.g., top, by the sealing layer and on every other side by the internal walls of the holder. In certain embodiments, the sealing layer is at least about 0.1 μm or thicker, and in certain embodiments ranges from about 0.01 to about 100 μm, such as from about 0.1 to about 50 μm, including from about 1 to about 10 μm. With respect to material from which the sealing layer may be fabricated, a number of different materials may be used including, but not limited to metals, e.g., noble metals and alloys thereof, such as described above, e.g., platinum, rhodium, iridium, and alloys thereof, metal suicides (e.g., as reviewed below), nitrides, e.g., aluminum nitrides, silicon nitrides, titanium nitride, carbides, etc. In one embodiment, the sealing layer (i.e., top cap metallization) is platinum or an alloy thereof. In another embodiment, the sealing layer is a dielectric, e.g., aluminum nitride, tungsten carbide, silicon carbide, etc.

In certain embodiments, a design is employed that mitigates the differences of coefficients of thermal expansion between the thick platinum metallization and the ceramic or silicon holder is provided. In this case, during the deposition of the platinum, the platinum is interlaced with an array of etched silicon or ceramic ribs in between. This design minimizes the total volume of material that is experiencing expansion and or contraction. The outside metallization can be platinum, or any noble metal, by example iridium, rhodium, or osmium, or alloys thereof.

An adhesion promoting layer may be included between the sealing layer and the holder which enhances adhesion of the sealing layer and holder. This adhesion promoting layer may vary, where suitable layers include, but are not limited to: titanium/tungsten, chromium, platinum oxide, and the like. Also of interest are silicides, e.g., as reviewed in greater detail below. The sealing layer can be adhered to the structure using a number of different protocols, including, but not limited to: diffusion bonding, welding, soldering, brazing, compression bonding, ultrasonic bonding, thermosonic bonding, thermocompression bonding, anodic bonding, etc.

In certain embodiments, the sealing layer is, in turn, coated with a dielectric, e.g., silicon carbide, silicon oxide, silicon nitride, etc.

The entire assembly can optionally be coated with a plastic, as desired.

Figure 2A:
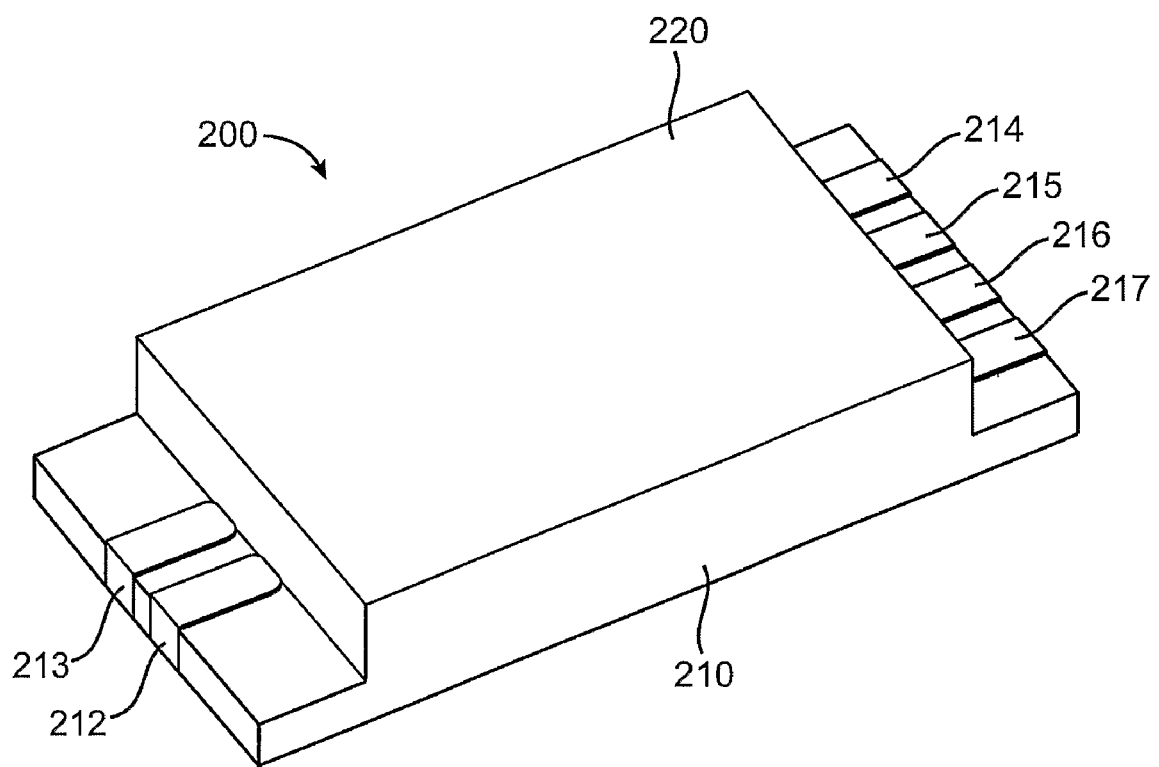
FIGS. 2A and 2B show different three-dimensional views of a hermetically sealed integrated circuit according to an embodiment of the invention.

FIG. 2A provides a three-dimensional view of a hermetically sealed structure according to an embodiment of the invention. In FIG. 2A, structure 200 includes holder 210 and sealing layer 220. Sealing layer 220 and holder 210 are configured to define a hermetically sealed volume (not shown) inside the holder. Also shown are external connector elements 212, 213, 214, 215, 216 and 217, which are coupled to conductive feedthroughs (not shown) present in the bottom of the holder.

Figure 2B:
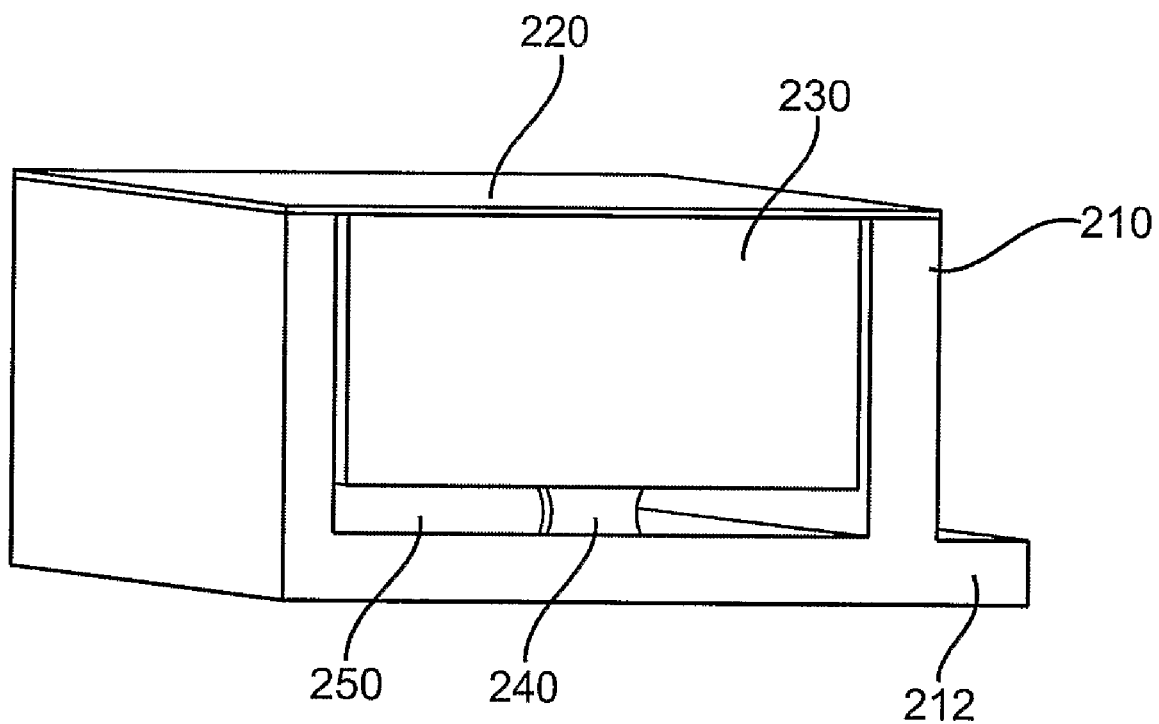

FIG. 2B provides a three-dimensional cut-away view of a hermetically sealed structure according to an embodiment of the invention. In FIG. 2B holder 210 and sealing layer 220 define a hermetically sealed volume 250 what holds an effector (e.g., comprising an integrated circuit) 230. The effector 230 is electrically coupled to the conductive (e.g., platinum) feedthroughs or vias 212 with a solder alloy (e.g., lead tin, gold tin, silver tin, or other suitable alloys) 240.

In certain embodiments, any space between an effector and the walls of the holder and/or sealing layer may be occupied by an insulating material. Any convenient insulating material may be employed, where representative insulating materials include, but are not limited to: liquids, e.g., silicon oil, elastomers, thermoset resins, thermoset plastics, epoxies, silicones, liquid crystal polymers, polyamides, polyimides, benzo-cyclo-butene, ceramic pastes, etc.

Figure 3A:
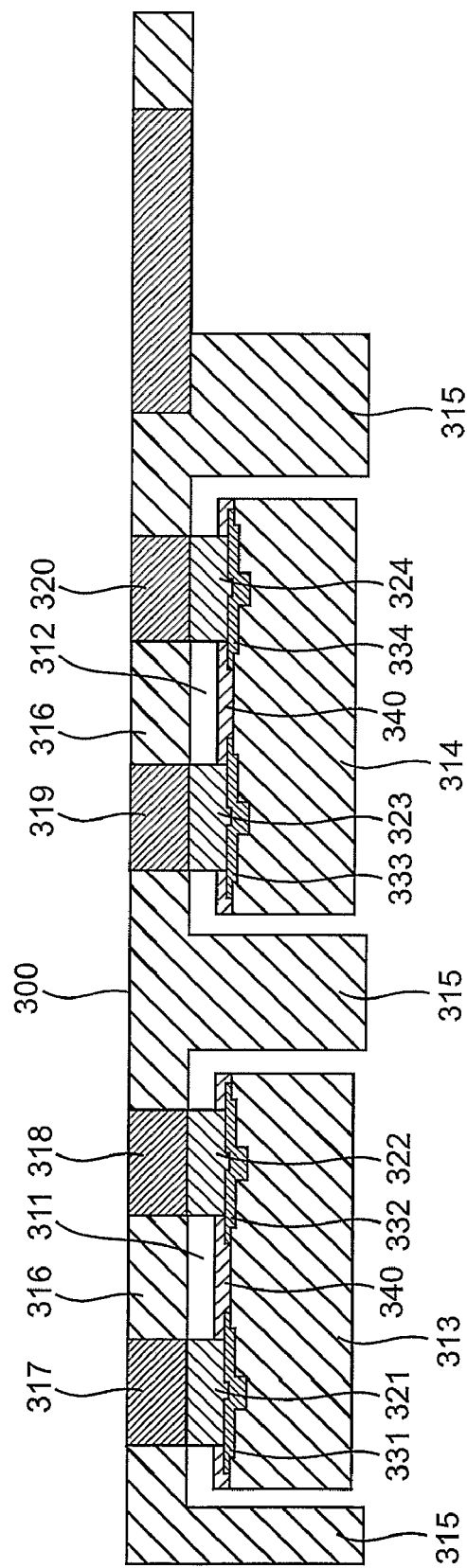
FIGS. 3A and 3B show different cross-sectional views of assemblies with multiple hermetically sealed integrated circuits according to alternative embodiments of the invention.

FIG. 3A provides a cross-sectional view of a hermetically sealed structure according to an embodiment of the invention. In this embodiment, the holder 300 includes two distinct wells 311 and 312, positioned side by side, e.g., in an array format, where each well houses two different effectors 313 and 314 (e.g., integrated circuits). Each well includes sides 315 and a bottom 316. Also shown in the bottom of each well are conductive feedthroughs 317, 318, 319 and 320. Electrically coupling the traces 331, 332, 333 and 334 of integrated circuits 313 and 314 to the conductive feedthroughs are solder connections 321, 322, 323 and 324. Separating the different solder connections from each other is insulating material 340. Although not shown, a suitable insulating material may also be present in the spaces between the effectors and the sides/bottom of the wells of the holder. In addition, a sealing layer is present on the surface opposite the feedthroughs, although not shown in FIG. 3A. While the depiction of FIG. 3A shows only two different integrated circuits hermetically sealed, structures of the invention may include many more integrated circuits, e.g., 4, 5, 6, or more circuits, in any convenient arrangement. One embodiment of the multiple chips per package design is to have a chip that is fabricated or otherwise designed to withstand higher voltages in one section of the assembly. The companion chip has a lower voltage tolerance than the first chip, but would not need the capacity of sustaining high voltages from cardiac pacing or other component demands from another part of the assembly. Both of those chips are dropped into the same hermetic packaging, e.g., in the same well or side by side wells, attached with a soldering process and then secured in place with an insulating material (i.e., potted), planarized or lapped back, e.g., as reviewed below, and then covered with a sealing layer.

While the above example provides guidance on synergistically providing two chips within a single inventive corrosion resistant hermetic package, these assemblies can handle up to 4, 5, 6, or more chips in a single assembly. In such larger scale assemblies, there is also the advantage that these assemblies can stacked on top of each other to add more functionality to the medical device components to be hermetically protected.

Figure 3B:
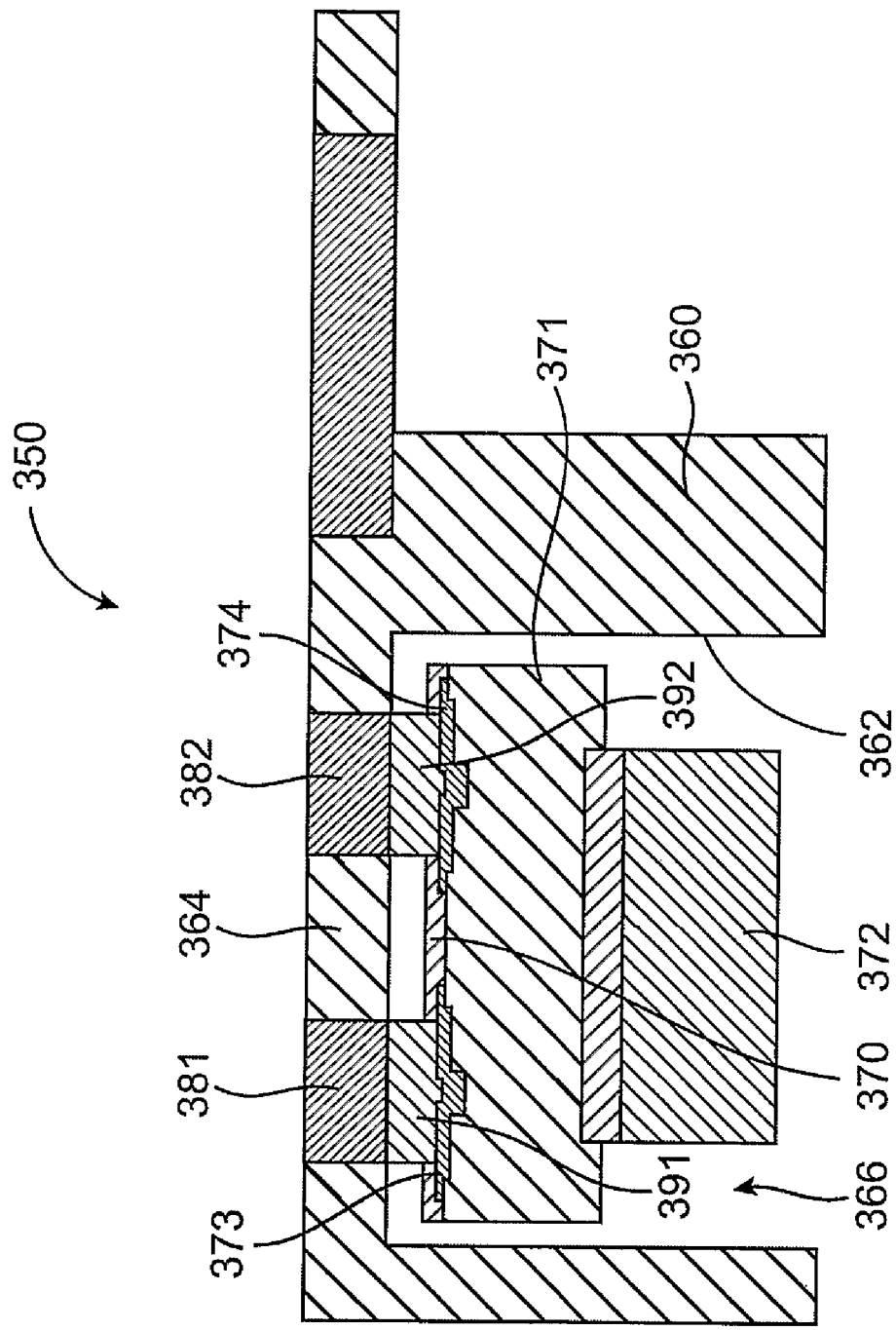

In FIG. 3B, structure 350 includes holder 360 with sides 362 and bottom 364 defining well 366. Present in well 366 are two different effectors 371 and 372 stacked on top of each other. Also shown in the bottom of each well are conductive feedthroughs 381 and 382. Electrically coupling the traces 373 and 374 of integrated circuit 371 to the conductive feedthroughs are solder connections 391 and 392. Separating the different solders from each other is insulating material 370. Although not shown, a suitable insulating material may also be present in the spaces between the effectors and the sides/bottom of the well of the holder. In addition, a sealing layer is present on the surface opposite the feedthroughs, although not shown in FIG. 3B.

Methods of Fabrication

Embodiments of the hermetically sealed structures may be fabricated using any convenient protocol. Aspects of these embodiments of the invention include placing one or more effectors in an in vivo corrosion resistant holder; and producing a sealing layer over the opening of the holder to seal the one or more effectors in the holder in a hermetically sealed volume. Depending on the nature of the effector, embodiments of the methods further include electrically coupling the effector to a conductive feedthrough present in the holder. Furthermore embodiments of the methods include making the corrosion resistant holders.

Any of a variety of different protocols may be employed in manufacturing the sealed structures and components thereof. For example, molding, deposition and material removal, e.g., planar processing techniques, such as Micro-Electro-Mechanical Systems (MEMS) fabrication, may be employed. Deposition techniques that may be employed in certain aspects of fabrication the structures include, but are not limited to: electroplating, cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner.

In a fabrication protocol according to an embodiment of the invention, the holder is first produced. As reviewed above, the holder can be fabricated from any of a variety of different materials, including but not limited to: silicon (single or polycrystalline), silicon carbide (single or polycrystalline), alumina, or other appropriate ceramics. The holder may be produced by a number of different protocols, including molding, as well as material removal/deposition protocols employed in the manufacture of MEMS devices, where certain protocols are further illustrated below.

In the bottom of the container one or more holes (e.g., in the form of trenches) may be produced which will be filled with a conductive material to produce the conductive feedthroughs. These holes or trenches can be produced by a number of approaches, including but not limited to: electronic discharge machining (EDM), reactive ion etching, grinding, chemical etching, The holes are filled with a conductive material, e.g., metal, metal silicide, etc., to produce conductive feedthroughs. The holes may be filled with the conductive material before or after the integrated circuit is positioned in the holder, depending on the particular protocol that is employed in fabrication of the structure. In certain embodiments, a base layer of a metal, e.g., platinum, is applied, such as through a sputtering process if this assembly is going to be built up through electroplating. The trenches are then filled in using an electroplating, plasma enhanced chemical vapor deposition process, or through other appropriate means. In yet other embodiments, as reviewed below, the integrated circuit is placed in the holder first, followed by filling in of the holes with a conductive material, e.g., a metal.

The integrated circuit may be positioned in the holder using any convenient protocol. In certain embodiments, in positioning the integrated circuit in the holder, the trace side of the integrated circuit die is positioned facing the bottom of holder so that electrical contact can be made between the traces of the circuit and the feedthrough(s) in the bottom of the holder. In one embodiment of the present invention, the integrated circuit may be covered with a thin film of one or more material, e.g., with a Pt thin film and then a silicon carbide film. Alternatively, in wafers that have through wafer vias, the wafer may be positioned trace side up in the holder and electrical connection made to the conductive feedthroughs of the holder by the through wafer vias.

In those embodiments where the bottom of the holder includes conductive feedthroughs prior to positioning of the chip in the holder, aspects of the methods include establishing an electrical connection between the circuitry of the integrated circuit and the conductive feedthroughs. In certain embodiments, electrical connection is established by providing a suitable solder material, e.g., gold, gold tin, or silver tin solder, present (e.g., bumped) on the surface. Following positioning of the integrated circuit in the holder such that the solder contacts the metallic feedthroughs, the resulting assembly is heated to above the melting point of the solder to form electrical contact with the feedthroughs in the holder.

In certain embodiments, remaining spaces present between the integrated circuit and walls/bottom of the holder may be filled with a suitable insulative material, e.g., polyimide, an epoxy or a low melting point glass, where the material is generally one that is compatible with the deposition process of the sealing layer, e.g., metal sealing layer, that follows.

At this point, the holder is sealed with a sealing layer in a manner such that the integrated circuit is sealed in a defined volume defined by the holder and the sealing layer. Generally, this step of the protocol of these embodiments includes producing a sealing layer across the surface of the structure opposite the bottom of the surface, which surface is defined by the tops of the walls of the holder, the bottom (non-circuit side) of the integrated circuit and any insulative material.

To ensure that a defect free sealing layer is produced in this step, the surface of the structure may be planarized, (i.e., lapped) to produce a uniform surface substantially free of any irregularities, e.g., bumps, cracks, etc. The uniform height of the resultant lapped surface allows the formation of a crack free protective layer. This step ensures that no irregularities are present on the surface that may adversely impact the structural integrity of the sealing layer that is produced on the top surface.

The surface, (i.e., top) of the resulting structure is then covered with a sealing layer, e.g. a sputtered Pt film. In certain embodiments, additional material may be plated onto the initial layer for enhanced thickness, e.g., where the sputtered film is then covered with Pt plating. In one embodiment of the present invention, the IC chip is covered with a Pt thin film and then a silicon carbide film.

The above protocol results in the production of a hermetically sealed integrated circuit. Where desired, any of the top, bottom or side surfaces of the structure may be further coated with an additional material, e.g., a dielectric such as silicon carbide, silicon oxide, silicon nitride, aluminum nitride, tungsten carbide, etc. In addition, both metal and dielectric layers may be present, stacked in any of variety of different sequences, as desired.

Figure 4A:
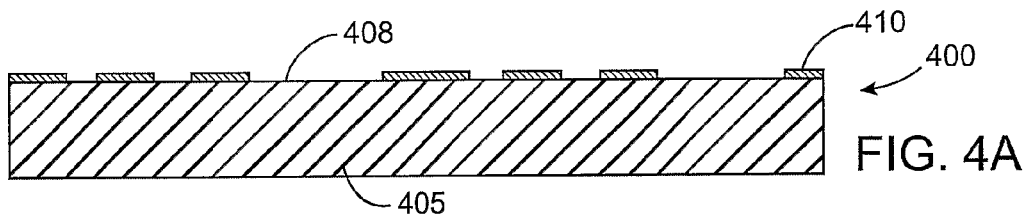
FIGS. 4A to 4M are diagrams showing a method for fabricating a hermetically sealed structure according to an embodiment of the invention.
Figure 4B:
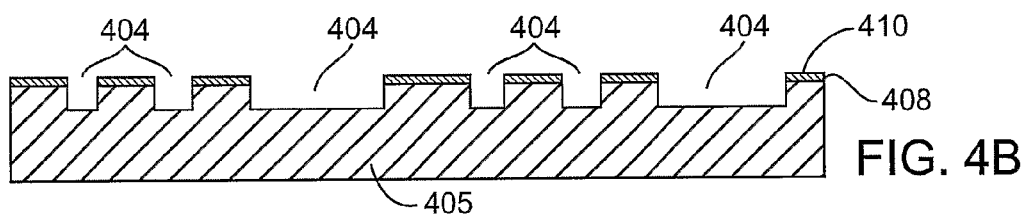
Figure 4C:
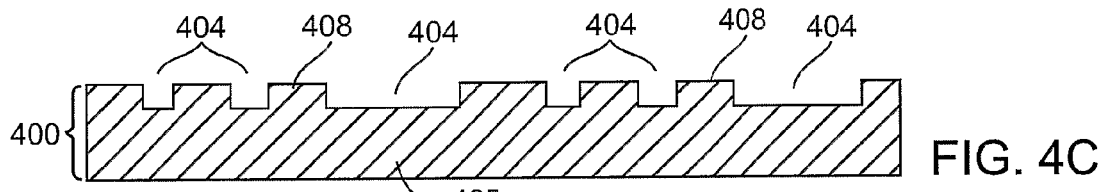
Figure 4D:
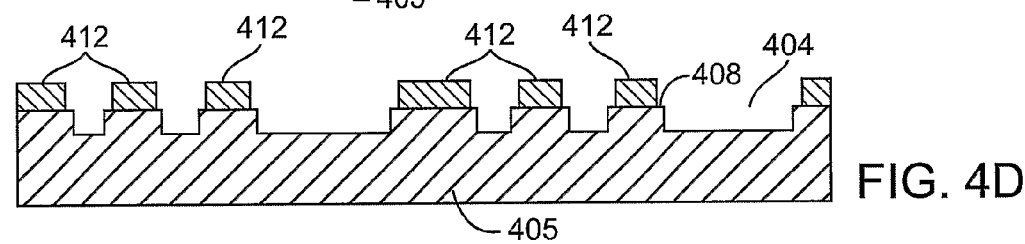
Figure 4E:
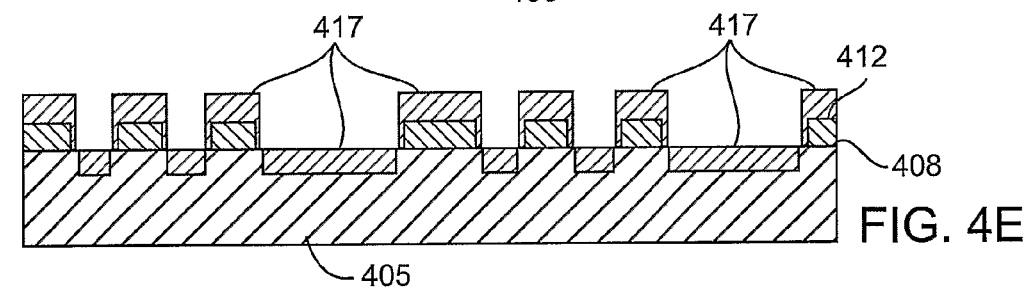
Figure 4F:
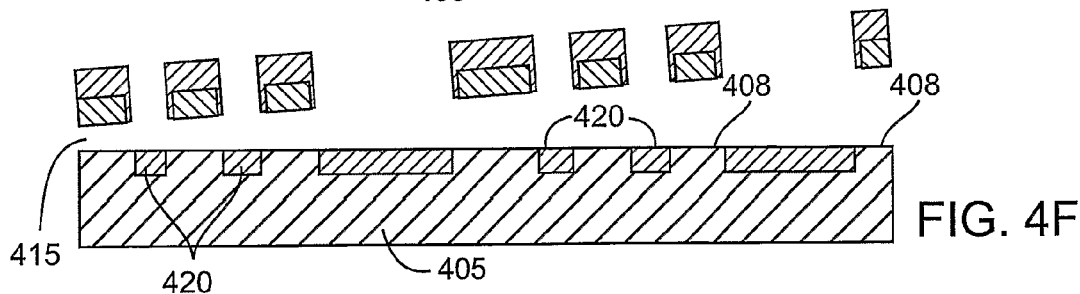
Figure 4G:
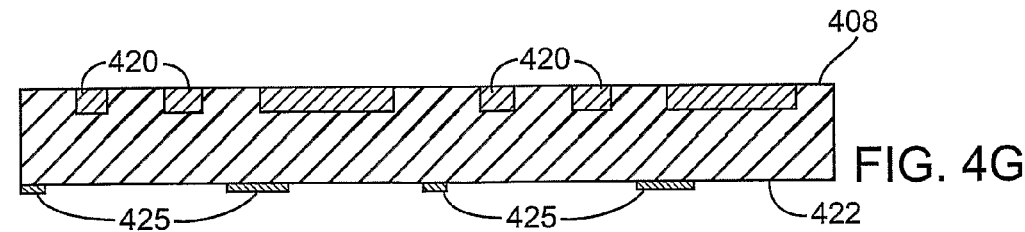
Figure 4H:
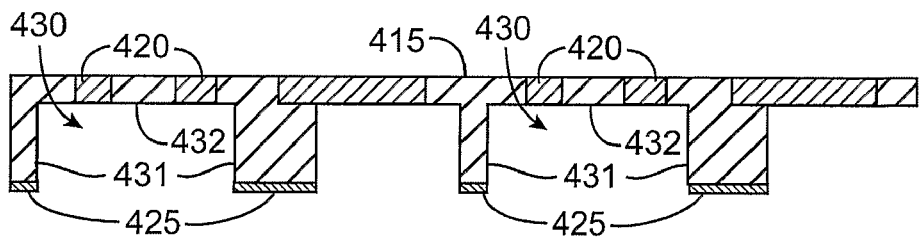
Figure 4I:
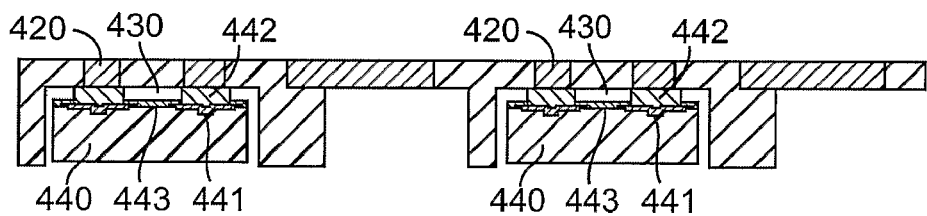
Figure 4J:
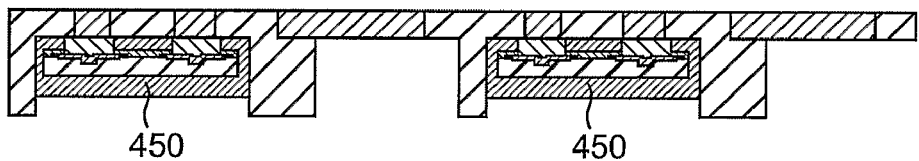
Figure 4K:
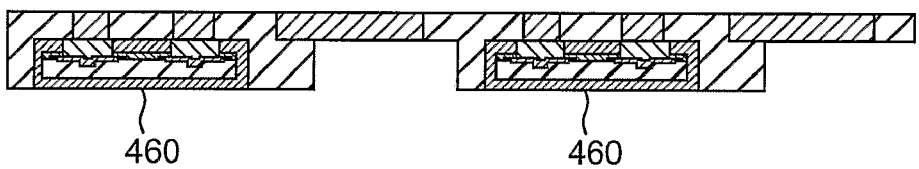
Figure 4L:
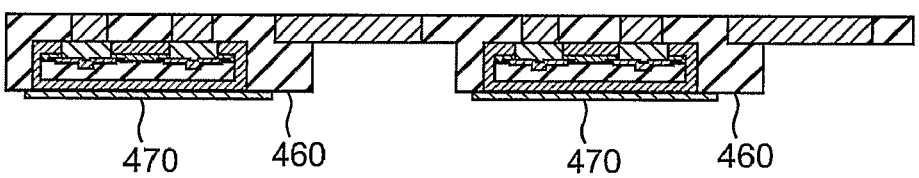
Figure 4M:
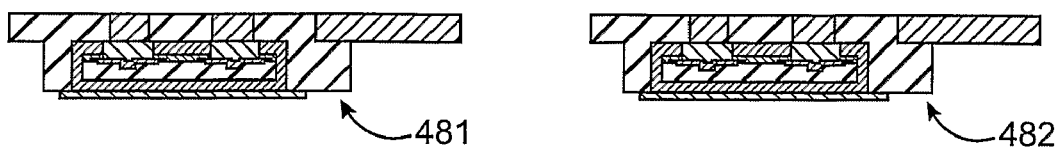

Representative fabrication protocols for producing various sensor structures described above are now discussed in greater detail. FIGS. 4A to 4M provide a flow diagram of a processing protocol according to an embodiment of the invention that can be employed to manufacture a hermetically sealed structure, which process may be referred to as a "shadow mask" process. In FIG. 4A, initial structure 400 includes base layer 405 (e.g., silicon, silicon carbide, etc.) which has mask layer 410 present on a first surface 408. Following removal of exposed material, e.g., via plasma etching techniques, shallow recesses 404 (e.g., in the form of trenches) are produced on first surface 408 as shown in FIG. 4B. These recesses will ultimately become the conductive feedthroughs, as shown below. Following removal of mask layer 410, structure 400 includes recesses 404 present on surface 408, as shown in FIG. 4C. Next, a shadow mask 412 is placed on the surface 408 of base layer 405 as shown in FIG. 4D. Shadow mask 412 may be produced using any convenient protocol, e.g., by reactive ion etching, photoetching or electroforming, etc. A conductive layer 417, e.g., of a metal, is then produced across the upper surface 408 and mask 412 of structure 400, as shown in FIG. 4E, e.g., via deposition, plating, etc. The conductive layer 417 completely fills recesses 404 on surface 408. Next, the mask layer 412 is planarized, as shown in FIG. 4F, leaving conductive elements 420 present on surface 408 of base 405. In FIG. 4G, mask layer 425 is produced on bottom surface 422. Next, material is removed from bottom surface 422 as shown in FIG. 4H. Following removal of backing layer 425, structure 400 may be considered a microfabricated chip package that includes: an array of feedthroughs fabricated, e.g., using planar processing techniques, and an array of cavities, e.g., fabricated using planar processing techniques. This step results in the production of holders 430 having side walls 431 and bottoms 432, where the bottoms 432 include conductive elements 420 which are now conductive feedthroughs, e.g., of a metal or a doped semiconductor material. FIG. 4I shows placement of integrated circuits 440 into holders 430, where the integrated circuit traces 441 are electrically isolated from each other by insulative material 443. Also shown are solders 442 which provide for electrical connection between traces 441 and conductive elements (i.e., feedthroughs) 420. Next, insulative material 450, e.g., epoxy, is introduced into holders 430 to fill any gaps between the integrated circuit and holder walls/bottom, as shown in FIG. 4J. In FIG. 4K, surface 422 has been planarized (i.e., lapped) to produce new planar surface 460 that is free of surface irregularities. FIG. 4L shows the production of sealing layer 470 on planar surface 460. In this figure, a structure is shown that includes an array of holders each with integrated feedthroughs, where each chip holder contains an integrated circuit, an insulative material fills the space between the integrated circuit and the walls of the holders. The structure is further characterized in that the insulative material, integrated circuits and array of chip holders has been planarized and a corrosion resistant material that covers the planarized array of chip holders is present. In a final step, structure 400 has been cleaved to produce hermetically sealed integrated circuits 481 and 482, as shown in FIG. 4M.

Figure 5A:
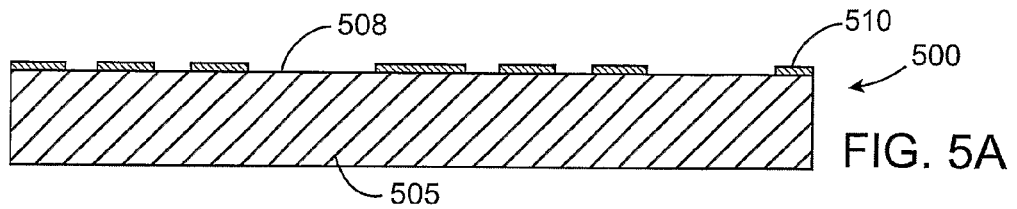
FIGS. 5A to 5L are diagrams showing a method for fabricating a hermetically sealed structure according to an embodiment of the invention.
Figure 5B:
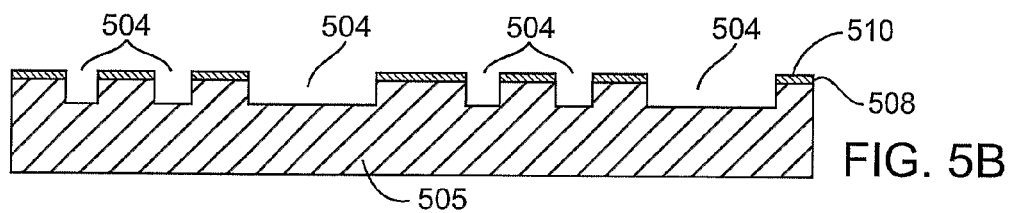
Figure 5C:
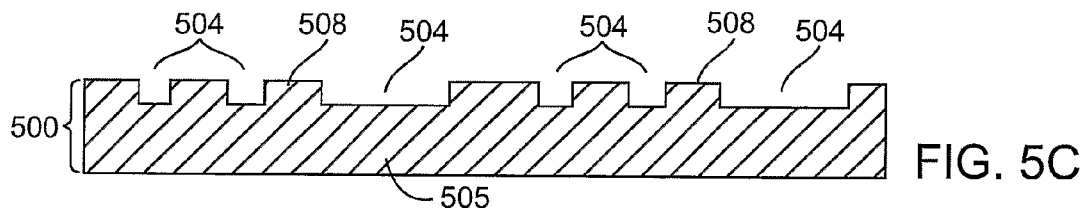
Figure 5D:
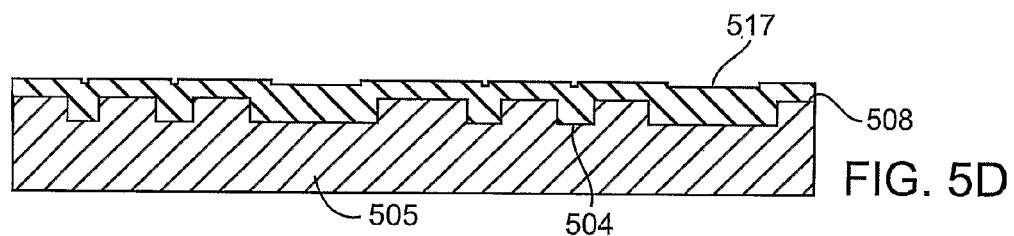
Figure 5E:
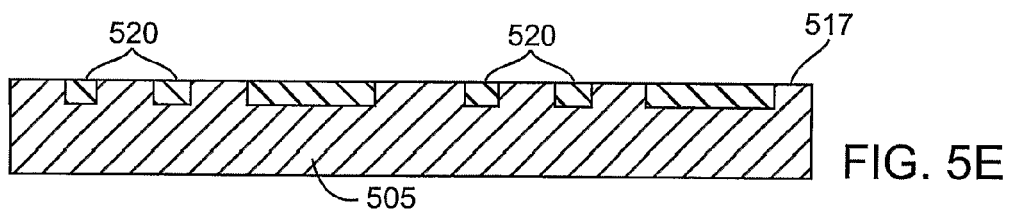
Figure 5F:
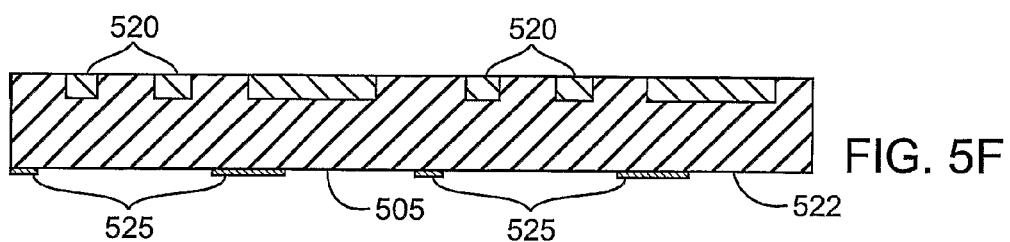
Figure 5G:
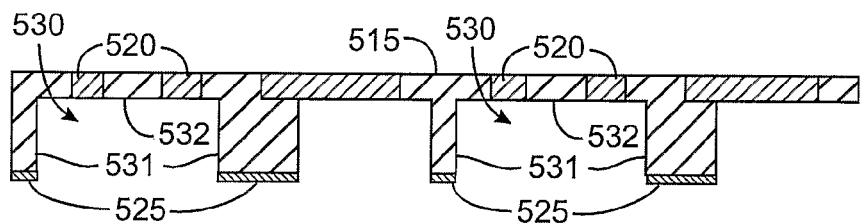
Figure 5H:
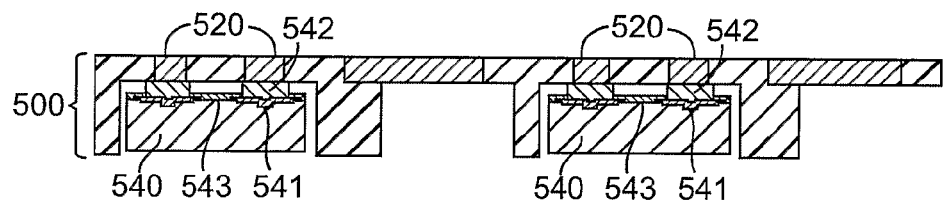
Figure 5I:
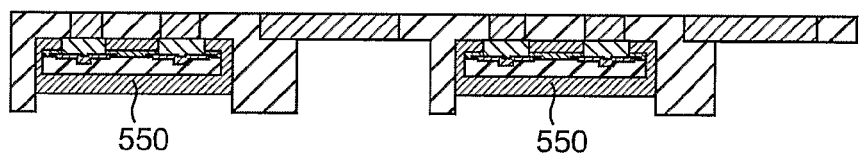
Figure 5J:
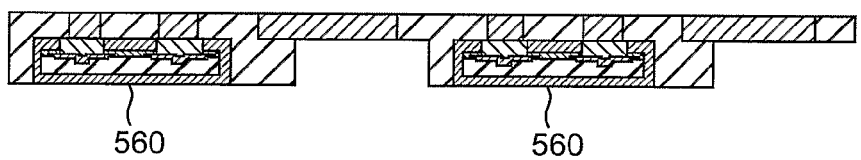
Figure 5K:
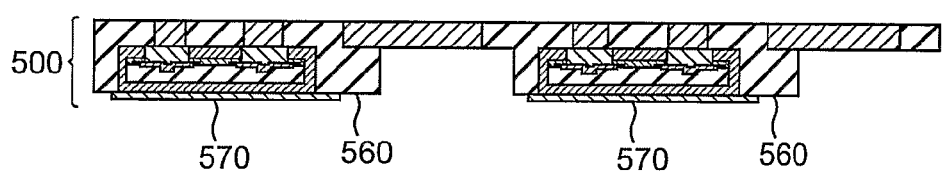
Figure 5L:
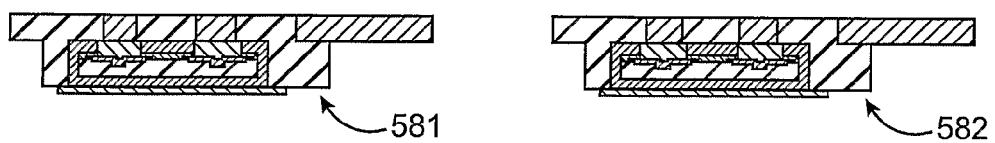

FIGS. 5A to 5L provide a flow diagram of a processing protocol according to an embodiment of the invention that can be employed to manufacture a hermetically sealed structure, which process may be referred to as a "damascene" process. In FIG. 5A, initial structure 500 includes base layer 505 (e.g., silicon, silicon carbide, etc.) which has mask layer 510 present on a first surface 508. Following material removal, e.g., via plasma etching techniques, shallow recesses 504 (e.g., in the form of trenches) are produced on first surface 508 as shown in FIG. 5B. These recesses will ultimately become the conductive feedthroughs, as shown below. Following removal of mask layer 510, structure 500 includes recesses 504 present on surface 508, as shown in FIG. 5C. Next, a conductive layer 517, e.g., of a metal, is then produced across the upper surface 508, as shown in FIG. 5D, e.g., via deposition, plating, etc. The conductive layer 517 completely fills recesses 504 on surface 508. Next, the top surface 515 is planarized, e.g., by lapping or chemical-mechanical polishing, etc., as shown in FIG. 5E, leaving conductive elements 520 present on surface 515 of base 505, such that surface 515 is planar. In FIG. 5F, mask layer 525 is produced on bottom surface 522. Next, material is removed from bottom surface 522 as shown in FIG. 5G. This step results in the production of holders 530 having side walls 531 and bottoms 532, where the bottoms 532 include conductive elements 520 which are now conductive feedthroughs. FIG. 5H shows placement of integrated circuits 540 into holders 530, where the integrated circuit traces 541 are insulated from each other by insulative material 543. Also shown are solders 542 which provide for electrical connection between traces 541 and conductive elements (i.e., feedthroughs) 520. In addition, mask layer 525 has been removed from bottom surface 522. Next, insulative material 550, e.g., epoxy, is introduced into holders 530 to fill any gaps between the integrated circuit and holder walls/bottom, as shown in FIG. 5I. In FIG. 5J, surface 522 has been planarized (i.e., lapped) to produce new planar surface 560 that is free of surface irregularities. FIG. 5K shows the production of sealing layer 570 on planar surface 560. In a final step, structure 500 has been cleaved to produce product hermetically sealed integrated circuits 581 and 582, as shown in FIG. 5L.

Figure 6A:
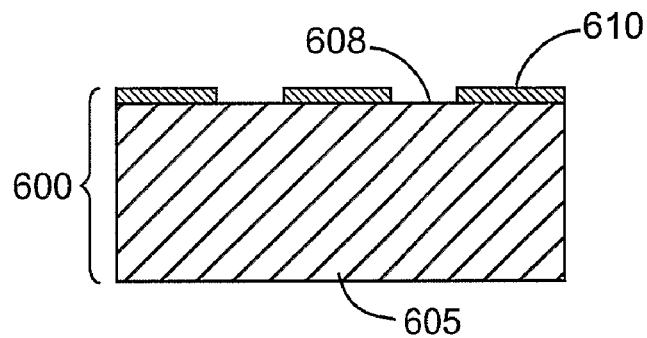
FIGS. 6A to 6H are diagrams showing a method for fabricating a hermetically sealed structure according to an embodiment of the invention.
Figure 6B:
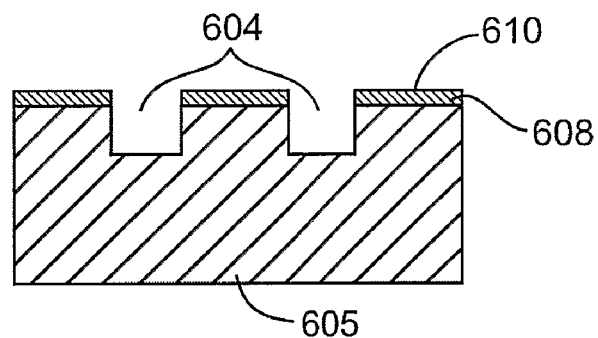
Figure 6C:
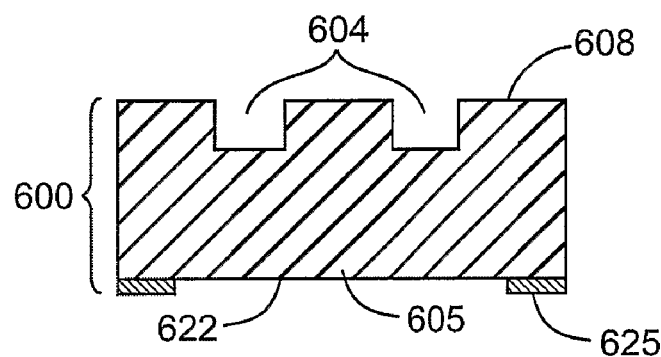
Figure 6D:
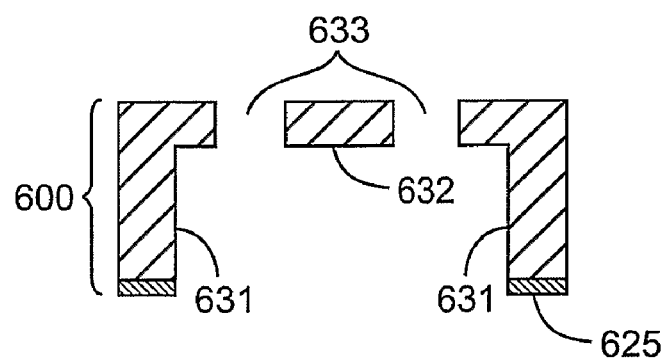
Figure 6E:
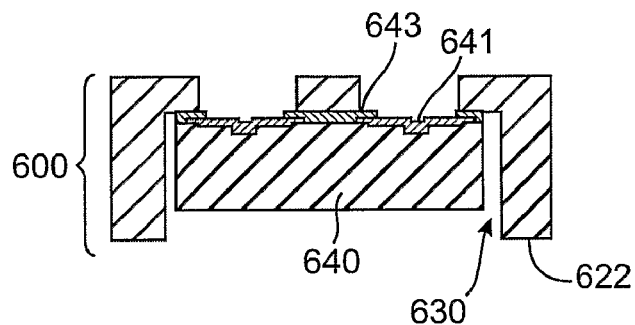
Figure 6F:
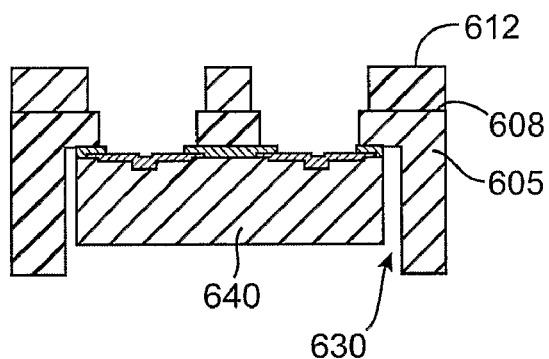
Figure 6G:
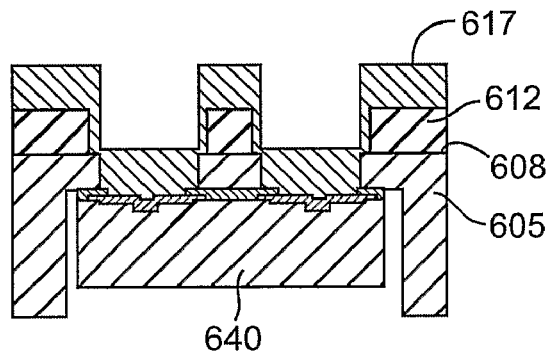
Figure 6H:
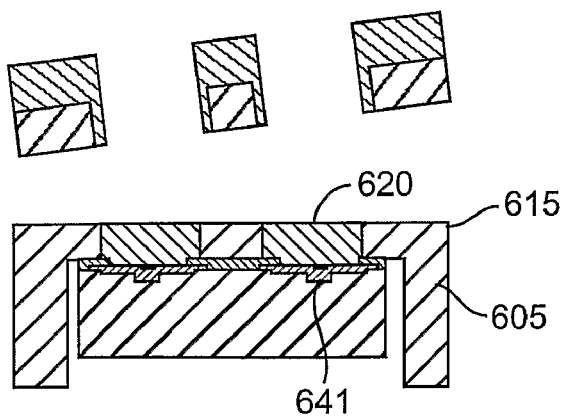

FIGS. 6A to 6L provide a flow diagram of a processing protocol according to an embodiment of the invention that can be employed to manufacture a hermetically sealed structure, which process may be referred to as a "solder-free" process. In FIG. 6A, initial structure 600 includes base layer 605 (e.g., silicon, silicon carbide, etc.) which has mask layer 610 present on a first surface 608. Following removal, e.g., via plasma etching techniques, shallow recesses 604 (e.g., in the form of trenches) are produced on first surface 608 as shown in FIG. 6B. These recesses will ultimately become the conductive feedthroughs, as shown below. Following removal of mask layer 610, structure 600 includes recesses 604 present on surface 608, as shown in FIG. 6C. In addition, a mask layer 625 is produced on bottom surface 622. Next, material is removed from bottom surface 622 as shown in FIG. 6D. This step results in the production of holder 630 having side walls 631 and bottom 632, where the bottom 632 includes holes 633. FIG. 6E shows placement of integrated circuit 640 into holders 630, where the integrated circuit traces 641 are insulated from each other by insulative material 643. In addition, mask layer 625 has been removed from bottom surface 622. Next, a second mask layer 612 is placed on the surface 608 of base layer 605 as shown in FIG. 6F. Next, a conductive layer 617, e.g., of a metal, is then produced across the upper surface 608, as shown in FIG. 6G, e.g., via deposition, plating, etc. The conductive layer 617 completely fills recesses 604 on surface 608. Next, the top surface 615 is planarized, as shown in FIG. 6H, leaving conductive feedthroughs 620 present on surface 618 of base 605, such that conductive feedthroughs 620 are in electrical communication with traces 641. The resultant structure is then processed further, e.g., as described above in connection with FIGS. 4A to 4M and FIGS. 5A to 5L.

It is noted that the above described methods of fabrication are merely illustrative of different protocols that can be employed to manufacture the hermetically sealed structures according to the invention.

Silicide Embodiments

As described above, certain embodiments include the use of alloys of metals and semiconductor materials, particularly metal silicides, in various components of the subject hermetically sealed structures. The interdiffusion of silicon, germanium, gallium and the like and many metals produces a corrosion-resistant yet conductive material. A subset of this group of materials, known as silicides, is formed between a metal and silicon compound (crystalline silicon, amorphous silicon, silicon carbide, silicon nitride) after an annealing step is performed at a typically elevated temperature in an inert environment. The metal and silicon containing material interdiffuse at the metal-Si interface to form a variety of new compounds depending upon the annealing temperature, annealing environment and annealing time. Of interest for this inventive biomedical packaging application are ruthenium, osmium, iridium, palladium and platinum silicides, among others. These silicides are typically of thicknesses in the range of from about 0.1 µm to about 0.5 µm but can range from about 0.01 µm to about 250 µm and are formed in certain embodiments between about 25° C. and about 1500° C. The formation of a silicide alters the material structure and, as such, its chemical and mechanical properties. In the subject hermetically sealed structures, metal suicides provide increased corrosion resistance and increased substrate adhesion for both thin-film and bulk materials that make up the structures.

A metal that has been converted into a silicide has increased corrosion resistance due to the material modification of its exposed surfaces for two reasons. First, though they remain electrically conductive, silicides form a protecting silicon dioxide layer at the surface. Secondly, the new material has very different electro-catalytic behavior than the base metal it was created from. The combination of the oxide layer and altered electro-catalytic behavior increases the impedance between the silicide and the solution. This increase in impedance reduces the current that is passed to the solution for a given applied voltage. Through Faraday's Law, this reduction in current is directly linked to the reduction of corrosion rate of the silicide.

As two embodiments of the invention, suicides can be both formed by annealing a thin metal film on a silicon substrate and a thin silicon film on metal substrate. Depending upon the relative thicknesses, the metal or silicon material can be completely or partially converted to a silicide. By controlling the starting volume of the metal and silicon, the stoichiometry of the resulting silicide can be tailored for a specific annealing temperature. This tailoring allows for the altering of material and electrical characteristics of the silicide and is another embodiment of the invention. If the annealing time is controlled, only the material immediately at the Si-metal interface may be turned to silicide. Silicides can be formed at temperatures as low as 25° C. As such, silicide processing steps are compatible with commercial CMOS circuits.

In another embodiment of the invention, silicide conductors can be patterned using a one-mask diffusion barrier. As silicides can form at the interface of a metal and silicon, any un-silicided metal can be removed post anneal with an etchant that is selective to the metal relative to the silicide. The same is true for any unsilicided silicon on a metal substrate.

Moreover, a conductive silicide layer's relative thinness (0.1 µm to 1 µm) makes it easy to deposit additional dielectric and metal diffusion barriers on top of the silicide to improve corrosion resistance further such as silicon carbide, silicon nitride, alumina, polyimide and other polymers, and further metal layers such as platinum or iridium. The additional layering of thin films on top of the patterned suicide conductors represents another embodiment of the invention.

The interdiffusion of the two materials also succeeds in improving the mechanical adhesion of the two materials to each other. A chemical bond results between the two materials which can be used in sealing, packaging, assembly, die and wafer-level bonding applications. For two additional embodiments of the invention, a metal seal ring can be patterned on a silicon chip or wafer and this ring, when formed into a silicide, can be used to bond the chip to either another silicon chip or wafer or bulk metal sheet. Either embodiment creates a sealed cavity that is protected by either bulk material or corrosion-resistant silicide. This process can be performed at the die or wafer level. This inventive packaging scheme represents a substantial improvement over prior packaging methods that depend on a polymer or an easily corroded material for proper sealing.

The coefficient of thermal expansion of a silicide may also be between that of the silicon and the metal. This reduces the thermal stress concentrations at the various material interfaces. Using a silicide material to attach a metal to silicon eliminates the need to use a dissimilar metal as an adhesion layer (i.e. Ti, TiW, Cr, or Au). This is attractive because these materials exhibit either poor corrosion behavior or bio-toxicity and should not be used within the human body.

The improved adhesion is not limited to thin film applications. In additional embodiments of the invention, bulk metal preforms in the range of thicknesses from about 25 µm to about 1000 µm thick, such as from about 50 µm to about 500 µm thick, can be inserted into recesses in silicon trenches or vias and annealed. The resulting thick silicide will be conductive, corrosion resistant and will provide sufficient thickness for the laser welding or soldering of electrical conductors. Analogously, silicon preforms can be used with bulk metal substrates.

Silicides undergo a volumetric expansion during formation. This fact can be used to ensure that that large trenches or through-hole vias in silicon are completely filled with silicide. Solid metal inserts can be positioned in silicon trenches via placement, formation or deposition and fully or partially silicided to form a strong bond with the surrounding silicon. The expansion and subsequent bond with the silicon wall of the silicide will eliminate any micro-gaps that may have been left unsealed during the positioning of the metal insert.

There exist eutectic compositions of semiconductors and the aforementioned metals that are substantially lower in melting point than the melting point of the semiconductor or the metal alone. Thus, it is possible to have the metal-semiconductor layer liquefy during formation and any method used to manipulate a fluid (i.e. surface tension, gravity, pressure) can be used to position or accumulate an alloy. This effect can be increased by the use of a diffusion barrier that the alloy will not wet. In one embodiment of the invention, liquid alloy will wick into areas of exposed silicon. This liquefaction will also eliminate any dog-boning or other irregularities at the exposed silicon trench topography that may have been formed during the metal or silicon deposition.

Devices and Systems

Aspects of the invention include devices and systems, including implantable medical devices and systems, that include the hermetically sealed structures according to embodiments of the invention. The devices and systems may perform a number of different functions, including but not limited to physiological parameter monitoring, pharmaceutical agent delivery, electrical stimulation, e.g., for medical purposes, analyte, e.g., glucose detection, etc.

The implantable medical devices and system may have a number of different components or elements, where such elements may include, but are not limited to: sensors (e.g., cardiac wall movement sensors, such as wall movement timing sensors), cardiac stimulation elements and related structures, e.g., pacing leads with electrodes disposed thereon; processing elements, e.g., for controlling timing of cardiac stimulation, e.g., in response to a signal from one or more sensors; telemetric transmitters, e.g., for telemetrically exchanging information between the implantable medical device and a location outside the body; drug delivery elements, etc. As such, the subject hermetically sealed structures may be operably coupled, e.g., in electrical communication with, components of a number of different types of implantable medical devices and system, where such devices and systems include, but are not limited to: physiological parameter sensing devices; drug delivery devices, electrical (e.g., cardiac) stimulation devices, etc.

In certain embodiments of the subject systems and devices, one or more hermetically sealed structures of the invention are electrically coupled via the conductive feedthrough to at least one elongated conductive member, e.g., an elongated conductive member present in a lead, such as a cardiovascular lead. In certain embodiments, the elongated conductive member is part of a multiplex catheter, e.g., as described in Published PCT Application No. WO 2004/052182 and U.S patent application Ser. No. 10/734,490, the disclosures of which are herein incorporated by reference. In some embodiments of the invention, the devices and systems may include onboard logic circuitry or a processor, e.g., present in a central control unit, such as a pacemaker can. In these embodiments, the central control unit may be electrically coupled to one or more hermetically sealed structures via one or more conductive members.

The subject hermetically sealed structures find use in any medical device and system in which it is desired to implant for an extended period of time a hermetically sealed structure. Devices and systems in which the subject hermetically sealed structures find use include, but are not limited to, those described in: WO 2004/066817 titled "Methods And Systems For Measuring Cardiac Parameters"; WO 2004/066814 titled "Method And System For Remote Hemodynamic Monitoring"; WO 2005/058133 titled "Implantable Pressure Sensors"; WO 2004/052182 titled "Monitoring And Treating Hemodynamic Parameters"; WO 2004/067081 titled "Methods And Apparatus For Enhancing Cardiac Pacing"; U.S. Provisional Patent Application 60/638,928 entitled "Methods and Systems for Programming and Controlling a Cardiac Pacing Device" filed Dec. 23, 2004; U.S. Provisional Patent Application No. 60/658,445 titled "Fiberoptic Cardiac Wall Motion Timer" filed Mar. 3, 2005; U.S. Provisional Patent Application No. 60,667,759 titled "Cardiac Motion Detection Using Fiberoptic Strain Gauges," filed Mar. 31, 2005; U.S. Provisional Patent Application No. 60/679,625 titled "de Minimus Control Circuit for Cardiac pacing and Signal Collection," filed May 9, 2005; U.S. Provisional Patent Application No. 60/706,641 titled "Deployable Epicardial Electrode and Sensor Array," filed Aug. 8, 2005; U.S. Provisional Patent Application No. 60/705,900 titled "Electrical Tomography" filed Aug. 5, 2005; U.S. Provisional Patent Application No. 60/707,995 titled "Methods and Apparatus for Tissue Activation and Monitoring" filed Aug. 12, 2005; U.S. Provisional Patent Application No. 60/707,913 titled "Measuring Conduction Velocity Using One or More Satellite Devices," filed Aug. 12, 2005. These applications are herein incorporated into the present application by reference in their entirety.

Three illustrative devices/systems in which the subject hermetically sealed structures find use include: cardiovascular function monitoring/pacing devices; blood analyte detection devices and systems; and vision restoration devices and systems. Each of these diverse illustrative types of devices and systems is now reviewed separately in greater detail.

Cardiovascular Devices/Systems

In certain embodiments, the implantable medical devices and systems which include the subject hermetically sealed structures are ones that are employed for cardiovascular applications, e.g., pacing applications, cardiac resynchronization therapy applications, etc.

Figure 7:
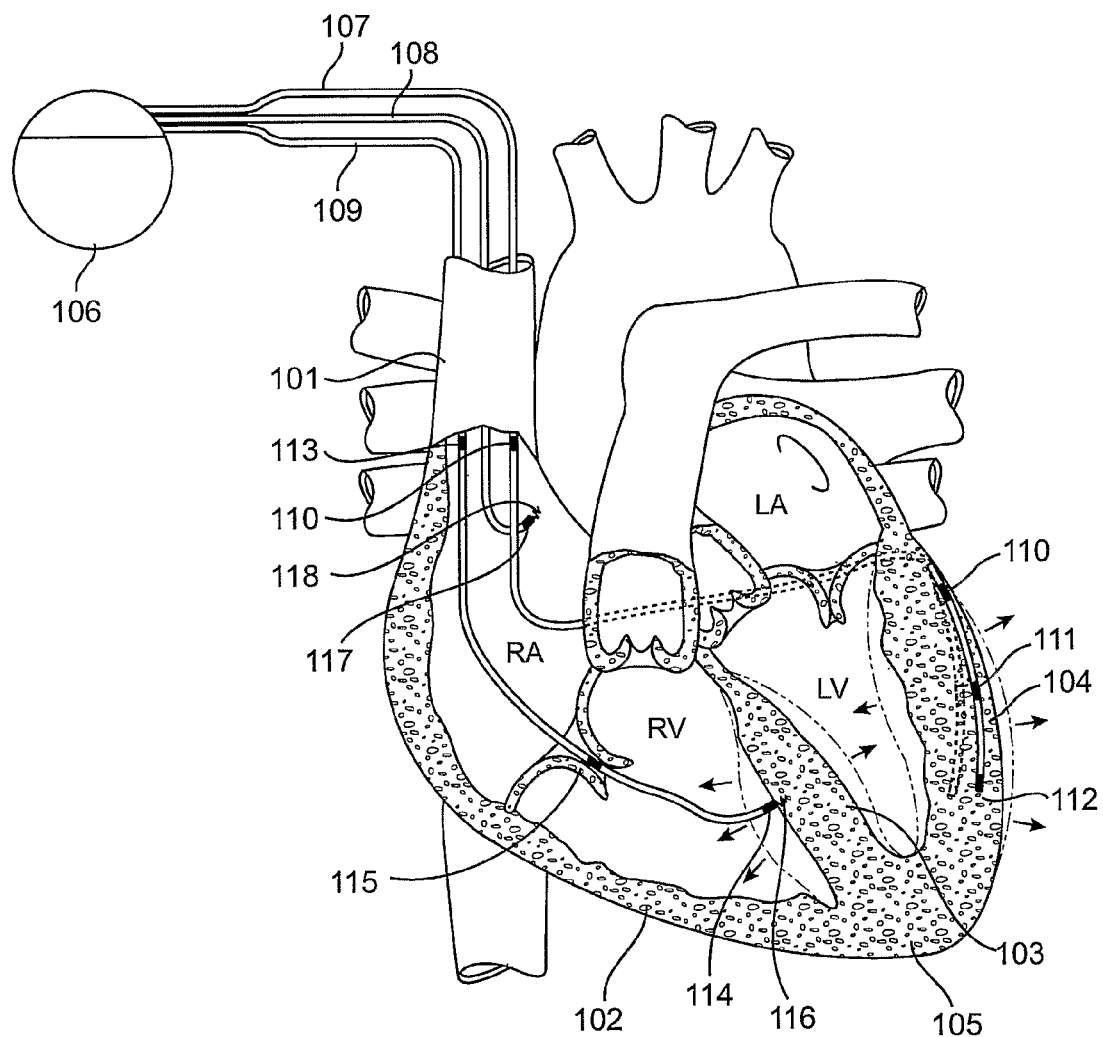
FIG. 7 provides a depiction of a cardiac resynchronization therapy system that includes one or more hermetically sealed integrated circuits coupled to lead electrodes according to an embodiment of the invention.

A representative system in which the hermetically sealed integrated structures find use is depicted in FIG. 7, which provides a cross-sectional view of the heart with of an embodiment of a cardiac resynchronization therapy (CRT) system that includes hermetically sealed integrated circuits according to embodiments of the invention. The system includes a pacemaker can 106, a right ventricle electrode lead 109, a right atrium electrode lead 108, and a left ventricle cardiac vein lead 107. Also shown are the right ventricle lateral wall 102, interventricular septal wall 103, apex of the heart 105, and a cardiac vein on the left ventricle lateral wall 104.

Figure 8:
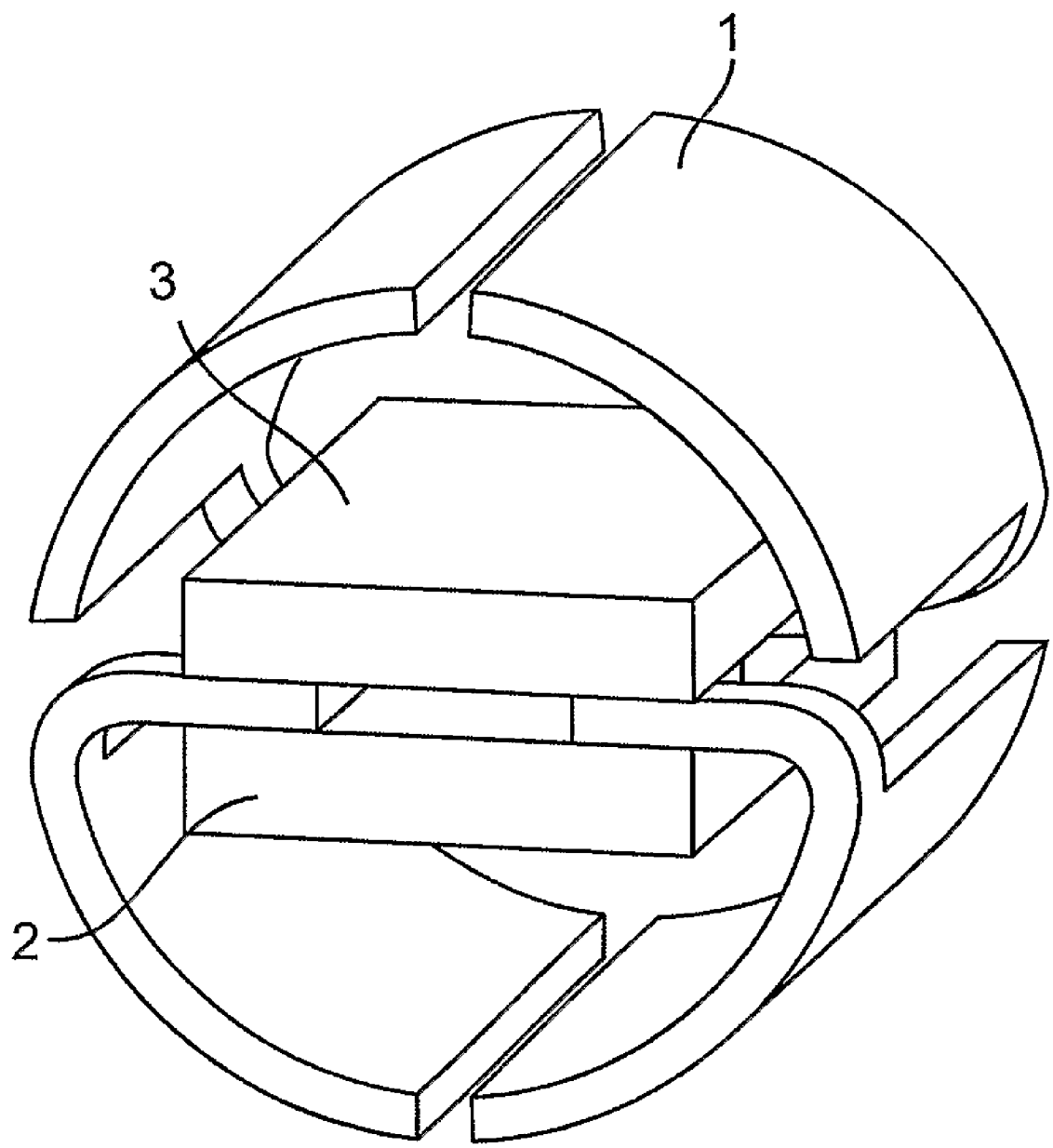
FIG. 8 provides a depiction of a lead electrode coupled to a hermetically sealed integrated circuit according to an embodiment of the invention.

The left ventricle electrode lead 107 is comprised of a lead body and one or more electrodes 110,111, and 112. Each of the electrodes includes a hermetically sealed integrated circuit, as shown in FIG. 8 below. Having multiple distal electrodes allows a choice of optimal electrode location for CRT. In a representative embodiment, electrode lead 107 is constructed with the standard materials for a cardiac lead such as silicone or polyurethane for the lead body, and MP35N for the coiled or stranded conductors connected to Pt—Ir (90% platinum, 10% iridium) electrodes 110,111 and 112. Alternatively, these device components can be connected by a multiplex system (e.g., as described in published U.S. Patent Application publication nos.: 20040254483 titled "Methods and systems for measuring cardiac parameters"; 20040220637 titled "Method and apparatus for enhancing cardiac pacing"; 20040215049 titled "Method and system for remote hemodynamic monitoring"; and 20040193021 titled "Method and system for monitoring and treating hemodynamic parameters; the disclosures of which are herein incorporated by reference), to the proximal end of electrode lead 107. The proximal end of electrode lead 107 connects to a pacemaker 106.

The electrode lead 107 is placed in the heart using standard cardiac lead placement devices which include introducers, guide catheters, guidewires, and/or stylets. Briefly, an introducer is placed into the clavicle vein. A guide catheter is placed through the introducer and used to locate the coronary sinus in the right atrium. A guidewire is then used to locate a left ventricle cardiac vein. The electrode lead 107 is slid over the guidewire into the left ventricle cardiac vein 104 and tested until an optimal location for CRT is found. Once implanted a multi-electrode lead 107 still allows for continuous readjustments of the optimal electrode location.

The electrode lead 109 is placed in the right ventricle of the heart with an active fixation helix at the end 116 which is embedded into the cardiac septum. In this view, the electrode lead 109 is provided with one or multiple electrodes 113,114, 115.

Electrode lead 109 is placed in the heart in a procedure similar to the typical placement procedures for cardiac right ventricle leads. Electrode lead 109 is placed in the heart using the standard cardiac lead devices which include introducers, guide catheters, guidewires, and/or stylets. Electrode lead 109 is inserted into the clavicle vein, through the superior vena cava, through the right atrium and down into the right ventricle. Electrode lead 109 is positioned under fluoroscopy into the location the clinician has determined is clinically optimal and logistically practical for fixating the electrode lead 109. Under fluoroscopy, the active fixation helix 116 is advanced and screwed into the cardiac tissue to secure electrode lead 109 onto the septum. The electrode lead 108 is placed in the right atrium using an active fixation helix 118. The distal tip electrode 118 is used to both provide pacing and motion sensing of the right atrium.

In FIG. 7 above, one or more of the electrodes of the system depicted in FIG. 7 is coupled to a hermetically sealed integrated circuit, as depicted in FIG. 8. FIG. 8 shows the configuration of electrodes around a hermetically sealed integrated circuit according to an embodiment of the invention. One of four electrodes 1 is distributed around the hermetically sealed IC 2 in a circumferential pattern. Electrode 1 is shown as a solid surface but it may have a finer scale pattern formed into the surface that improves the flexibility of the electrode. IC chip 2 is hermetically sealed and provides a multiplexed connection to conductors in the lead (not shown in this figure). Optionally, top cap 3 is bonded to the integrated circuit. Cap 3 is a component that helps support the electrode to integrated circuit connection. Cap 3 may contain additional circuits or sensors. This assembly would be incorporated into a flexible polymeric material to form the body of the device. The device may be round. It may also be some other shape best suited to the particular location in the body where is it would be used. Additional electrode structures in which the subject hermetically sealed integrated circuits find use include, but are not limited to: U.S. Provisional Patent Application Ser. No. 60/638,692 filed Dec. 22, 2004; U.S. Provisional Patent Application Ser. No. 60/655,609 filed Feb. 22, 2005; U.S. Provisional Patent Application Ser. No. 60/655,609 filed Feb. 22, 2005; U.S. Provisional Patent Application Ser. No. 60/751,111 filed Dec. 15, 2005 titled "Fatigue Resistant IC Chip Connection," and PCT application serial no. PCT/US2005/046811 filed on Dec. 12, 2005 and titled " IMPLANTABLE ADDRESSABLE SEGMENTED ELECTRODES"; the disclosures of which are herein incorporated by reference.

Analyte Detection Devices and Systems

Yet another type of medical device and system in which embodiments of the hermetically sealed structures of the invention find use is analyte detection devices, such as blood analyte detection devices, e.g., blood glucose detection devices. A variety of different light-based, e.g., infrared or near-infrared light based, analyte detection devices have been developed which include a light source, e.g., an infrared or near infra-red light source, for illuminating a fluid sample, e.g., blood, and a detector for detecting return light, e.g., reflected, refracted, etc., from the sample, where signals generated by the detector in response to light from the sample are processed (e.g., by comparing to a reference or control) to detect, either qualitatively or quantitatively, one or more analytes in the sample, e.g., glucose in a blood sample. Infrared or near-infrared blood analyte detection devices which may be adapted to include the hermetically sealed structures, e.g., containing an infrared light source and/or detector, include, but are not limited to, those described in U.S. Published Application Nos. 20040206905; 20040077950; 20040024321; 20020193671; 20020067476; 20020027649; 20050267346; 20050192493; 20050171413; 20050131286; 20050124869; 20050043603; 20050027183; 20040242977; 20040220458; 20040193031; 20040162470; 20040133086; 20040106163; 20030220581; 20030191377; 20030105391; 20030100846; 20030076508; 20030050541; 20030032885; 20030023152; 20030013947; 20020193673; 20020173709; 20020103423; 20020091324; 20020084417; 20020082487; 20020072658; 20020055671; 20020041166; 20020038080; 20020035341; 20020026106; 20020019055; 20020016534; 20010018560; the disclosures of which are herein incorporated by reference. Many of the above published applications describe devices and systems which are not implantable devices or systems. The present hermetically sealed structures allow these devices and systems to be readily modified to implantable format. For example, an implantable optical-based blood glucose analyte detection device is provided in certain embodiments of the invention in which the light source, e.g., infrared light source, is hermetically sealed in a silicon holder which is transparent to infrared light. The hermetically sealed light source is placed on a first side of a suitable blood vessel, such that light from the sealed light source can illuminate blood in the vessel. On the opposing side of the blood vessel is placed a hermetically sealed detector, which detector detects light from blood present in the vessel and generates electrical signal in response thereto. The hermetically sealed light source and detector are each coupled to a control unit, e.g., via at least one conductor, which provides actuation signals to the light source and receives signals from the detector, e.g., for subsequent processing, for example to qualitatively or quantitatively determine analyte, e.g., glucose, in blood in the vessel.

Vision Restoration Devices and Systems

Yet another type of medical device and system in which the subject hermetically sealed structures find use is vision restoration devices and systems, e.g., devices and systems that include implantable photodetector elements that convert detected light to electrical signals, e.g., for stimulating the optic nerve. For example, integrated circuits and photosensors, e.g., photovoltaic cells, can be hermetically sealed according to embodiments of the invention, e.g., in structures sufficiently transparent to wavelengths of interest, to provide for long term implantability of the devices and systems. Representative implantable vision restoration devices and systems in which the subject hermetically sealed structures may be incorporated include, but are not limited to those devices and systems described in: U.S. Pat. Nos. 4,628,933; 5,042, 223; 5,397,350; and 6,230,057; as well as in Published PCT Application Publication Nos. WO 01/74444 titled "Multi- Phasic Microphotodetector Retinal Implant With Variable Voltage And Current Capability And Apparatus For Insertion"; WO 01/83026 titled "Artificial Retina Device With Stimulating And Ground Return Electrodes Disposed On Opposite Sides Of The Neuroretina And Method Of Attachment"; WO 03/002190 titled "Methods For Improving Damaged Retinal Cell Function; WO 03/002070 titled "Methods For Improving Damaged Retinal Cell Function Using Physical And/Or Mechanical Stimulation"; WO 2004/071338 titled "Implantable Device Using Diamond-Like Carbon Coating"; WO 2004/112893 titled "Implant Instrument"; WO 2005/004985 titled "Treatment Of Degenerative Retinal Disease Via Electrical Stimulation Of Surface Structures"; WO 2005/004985 titled "Device For Treatment Of Degenerative Retinal Disease Via Electrical Stimulation Of Surface Structures Of The Eyeball"; and WO 2005/110326 titled "Mechanically Activated Objects For Treatment Of Degenerative Retinal Disease."

Kits

Also provided are kits that include the subject hermetically sealed structures, as part of one or more components of an implantable device or system, such as the devices and systems reviewed above. In certain embodiments, the kits further include at least a control unit, e.g., in the form of a pacemaker can. In certain of these embodiments, the structure and control unit may be electrically coupled by an elongated conductive member. In certain embodiments, the hermetically sealed structure may be present in a lead, such as a cardiovascular lead.

In certain embodiments of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An implantable hermetically sealed structure dimensioned to be placed inside a lead, the structure comprising:
   an in vivo corrosion resistant holder comprising:
      a plurality of in vivo corrosion resistant walls ("walls"), each wall in the plurality of walls comprising a top edge, adjoining edges, and a bottom edge, each adjoining edge of each wall in the plurality of walls physically associated with a respective adjoining edge of a respective wall in the plurality of walls to form a first opening at one end and a second opening at an opposite end;
      a bottom physically associated with the bottom edge of each wall in the plurality of walls to cap the first opening at one end of the in vivo corrosion resistant holder; and
      at least one conductive feedthrough extending through the bottom; and
   a metallic sealing layer physically associated with the top edge of each wall in the plurality of walls to substantially cap the second opening at an opposite end and to define a volume capable of accommodating an effector, whereby the metallic sealing layer, the in vivo corrosion resistant holder, and the at least one conductive feedthrough in combination are operable to hermetically seal the effector.

2. The implantable hermetically sealed structure according to claim 1, further comprising the effector.

3. The implantable hermetically sealed structure according to claim 2, wherein the effector further comprises at least one of an integrated circuit and an actuator.

4. The implantable hermetically sealed structure according to claim 3, wherein the actuator further comprises an electrode.

5. The implantable hermetically sealed structure according to claim 1, wherein the hermetically sealed structure is configured to remain hermetically sealed in a saline environment for at least 10 years.

6. The implantable hermetically sealed structure according to claim 1, wherein the in vivo corrosion resistant holder comprises at least two conductive feedthroughs.

7. The implantable hermetically sealed structure according to claim 1, wherein the conductive feedthrough is a metal.

8. The implantable hermetically sealed structure according to claim 1, wherein the corrosion resistant holder comprises silicon.

9. The implantable hermetically sealed structure according to claim 1, wherein the corrosion resistant holder is fabricated using a planar processing protocol.

10. The implantable hermetically sealed structure according to claim 1, wherein the structure further comprises an insulative material present within the opening.

11. An implantable medical device comprising a hermetically sealed structure according to claim 1.

12. The implantable medical device according to claim 11, further comprising the effector.

13. The implantable medical device according to claim 11, wherein the structure is present in a lead.

14. The implantable medical device according to claim 13, wherein the lead is a cardiovascular lead.

15. The implantable medical device according to claim 14, wherein the lead is a left ventricular lead.

16. The implantable medical device according to claim 14, wherein the lead is an epicardial lead.

17. The implantable medical device according to claim 11, wherein the structure is present in an implant.

18. The implantable medical device according to claim 17, wherein the implant is a cardiovascular implant.

19. The implantable medical device according to claim 11, wherein the device is chosen from a neurological device, a muscular device, a gastrointestinal device, a skeletal device, a pulmonary device, an ophthalmic device and an auditory device.

20. The implantable medical device according to claim 11, wherein the at least one conductive member is electrically coupled to a control unit.

21. The implantable medical device according to claim 20, wherein the control unit is present in a pacemaker can.

22. The implantable medical device according to claim 21, wherein the device is a cardiovascular pacing device.

23. The implantable medical device according to claim 11, wherein the device comprises two or more of the hermetically sealed structures.

* * * * *